US012667274B2

(12) United States Patent
Hagmeijer et al.

(10) Patent No.: US 12,667,274 B2
(45) Date of Patent: Jun. 30, 2026

(54) METHOD AND SYSTEM FOR DETERMINING A SCALED RESPIRATORY FLOW RATE AND VOLUME DURING RESPIRATION OF A PATIENT

(71) Applicant: UNIVERSITEIT TWENTE, Enschede (NL)

(72) Inventors: Rob Hagmeijer, Enschede (NL); Rutger Hendrik Johan Hebbink, Enschede (NL)

(73) Assignee: UNIVERSITEIT TWENTE, Enschede (NL)

( * ) Notice: Subject to any disclaimer, the term of this patent is extended or adjusted under 35 U.S.C. 154(b) by 353 days.

(21) Appl. No.: 18/028,998

(22) PCT Filed: Sep. 27, 2021

(86) PCT No.: PCT/NL2021/050582
§ 371 (c)(1),
(2) Date: Mar. 28, 2023

(87) PCT Pub. No.: WO2022/066017
PCT Pub. Date: Mar. 31, 2022

(65) Prior Publication Data
US 2023/0363666 A1 Nov. 16, 2023

(30) Foreign Application Priority Data
Sep. 28, 2020 (NL) ..................................... 2026553

(51) Int. Cl.
*A61B 5/087* (2006.01)
*A61B 5/00* (2006.01)
*A61B 5/091* (2006.01)

(52) U.S. Cl.
CPC .............. *A61B 5/087* (2013.01); *A61B 5/091* (2013.01); *A61B 5/742* (2013.01); *A61B 2562/0247* (2013.01)

(58) Field of Classification Search
CPC ......... A61B 5/087; A61B 5/091; A61B 5/742; A61B 2562/0247; A61B 2560/0257; A61B 5/097; A61B 5/6819
See application file for complete search history.

(56) References Cited

U.S. PATENT DOCUMENTS

2007/0125379 A1* 6/2007 Pierro ............... A61M 16/0666
128/204.23
2010/0252042 A1* 10/2010 Kapust .............. A61M 16/0858
128/207.18
2023/0245741 A1* 8/2023 Shigyo ................... G16H 20/70
705/2

FOREIGN PATENT DOCUMENTS

WO 2017020068 A1 2/2017
WO 2018215483 A1 11/2018

OTHER PUBLICATIONS

International Search Report and Written Opinion mailed Jan. 21, 2022, for Application No. PCT/NL2021/050582 (13 pages).

* cited by examiner

*Primary Examiner* — Jeffrey G. Hoekstra
(74) *Attorney, Agent, or Firm* — KDW Firm PLLC

(57) ABSTRACT
A method for determining a scaled respiratory flow rate and volume during respiration of a patient includes a) successively determining a plurality of values for a difference between a pressure in at least a first location in an upper respiratory tract of the patient and a reference pressure, b) deriving the scaled respiratory flow rate from the plurality of values for the pressure difference by using a first relationship, c) deriving the scaled respiratory volume from the plurality of values for the pressure difference by using a second relationship, and d) displaying the scaled respiratory flow rate derived in step b) and the scaled respiratory volume derived in step c) or a further variable derived from the scaled respiratory flow rate and volume in a graphical representation. Step a) is performed during tidal breathing of the patient. A system for performing the aforementioned method.

20 Claims, 6 Drawing Sheets

METHOD AND SYSTEM FOR DETERMINING A SCALED RESPIRATORY FLOW RATE AND VOLUME DURING RESPIRATION OF A PATIENT

This application is a national stage filing under 35 U.S.C. 371 of pending International Application No. PCT/NL2021/050582, filed Sep. 27, 2021, which claims priority to Netherlands Patent Application No. 2026553, filed Sep. 28, 2020, the entirety of which applications are incorporated by reference herein.

The invention relates to a method for determining a scaled respiratory flow rate and volume during respiration of a patient. The method may be used to obtain tidal spirometric curves.

Spirometry is a gold standard to diagnose pulmonary diseases. In a spirometry test, flow-volume curves are obtained by letting the patient inhale to his maximum ability and then forcefully exhale through a mouth piece. The shape of the flow-volume curves can be used as an indication of several pulmonary diseases such as bronchiolitis and COPD. A drawback of spirometry is that patients have to be able to conduct the required respiration maneuvers. Especially the required effort for the forceful exhaling maneuver may be problematic for patients with severe pulmonary diseases and for elderly people. Furthermore, spirometry tests on infants may be difficult due to a lack of patient cooperation.

Though not a gold standard, pulmonary diseases can also be diagnosed by tidal spirometry. Evidence for the influence of pulmonary diseases on tidal breathing patterns has been presented in several studies on both infants and adults. To obtain tidal spirometric curves, pneumotachography (PNT) is used, in which patients are connected to a face mask or to a combination of a mouthpiece and a nose clip, and the time dependent flow rate is measured by a pneumotachograph. A major drawback of this technique is that respiratory behaviour is altered because of the required face mask or mouth piece. Another drawback is encountered for neonates, where the dead space of the apparatus may exceed the infant's own dead space, limiting the time of measurement.

An alternative way to record tidal breathing is by the use of nasal cannula, as used in for example nasal high-flow therapy (NFHT). This idea was used in studies to record respiratory events during sleep, and used to determine inspiratory flow limitation. Although the inspiratory flow rate could not be quantified, it was assumed to be linearly dependent on the nasal cannula pressure, and flow limitation was detected by plotting the nasal cannula pressure versus the driving (supraglottic or esophageal) pressure. However, a major drawback of this method is that it is invasive and patient-unfriendly because of the need for an esophageal or supraglottic catheter.

The invention has for its object to provide a method of the type discussed above in which the above-mentioned drawbacks are obviated at least to some extent. To this end the invention provides a method for determining a scaled respiratory flow rate and volume during respiration of a patient, comprising the steps of:

a) successively determining a plurality of values for a difference between a pressure in at least a first location in an upper respiratory tract of the patient and a reference pressure;

b) deriving the scaled respiratory flow rate from the plurality of values for the pressure difference by using a first relationship;

c) deriving the scaled respiratory volume from the plurality of values for the pressure difference by using a second relationship; and d) displaying the scaled respiratory flow rate derived in step b) and the scaled respiratory volume derived in step c) or a further variable derived from the scaled respiratory flow rate and volume in a graphical representation;

wherein step a) is performed during tidal breathing of the patient.

By focusing the determination of the pressure difference on the upper part of the respiratory tract, there is no need for using a catheter. Performing the determination during tidal breathing obviates the need for maximum inhalation and forceful exhalation. And by displaying a graphical representation of the results of the method, they may be quickly and easily analysed. In addition to or instead of displaying the scaled respiratory flow rate and volume, the method may also include deriving a further variable from the scaled respiratory flow rate and volume, and dispaying this further derived variable. Such a variable could e.g. be the FEV1, which may also serve to characterize a patient's breathing.

In an embodiment of the method the scaled respiratory flow rate and scaled respiratory volume may be displayed in a single graph. This single graph may be a tidal spirometric curve or flow-volume curve. This type of curve is a well-known and widely used tool for analysis and diagnosis of respiratory disorders.

In an embodiment of the method the first and second relationships used in steps b) and c) are each generalized relationships which are substantially independent of the patient. The use of generalized relationships allows the respiratory flow and volume to be determined relatively swiftly and easily. By "generalized" and "substantially independent of the patient" it is meant that the forms of the relationships are general, although the actual values of some constants appearing in these relationships (to be discussed below) are still patient-specific. The relationships may be generalized and made substantially independent of a particular patient by scaling. As a result of such scaling, two of the patient-specific constants appear only as a ratio, rather than individually.

In order to improve the detection of the pressure difference an obstacle may be arranged in the upper respiratory tract before step a) is performed. Such an obstacle causes a local narrowing of the respiratory tract, which in turn leads to a viscous pressure loss of the airflow, causing a greater pressure difference with the reference pressure.

In an embodiment of the method the first location in the upper respiratory tract may be in a nostril of the patient and the reference pressure may be ambient pressure. The nostril is at the very beginning of the respiratory tract and is easily accessible, while ambient pressure is easy to measure and thus forms a good reference.

In order to obtain a detectable pressure difference immediately at the beginning of the respiratory tract the obstacle may be arranged in the nostril between the first location and a nostril entry.

In an embodiment of the method there may be a first location in each of the patient's nostrils and a first plurality of values for the pressure difference may be determined in one of the patient's nostrils, while a second plurality of values for the pressure difference may be determined in the other nostril. In this way there are two series of measurements, which may be compared to check the integrity and robustness of data collected during the measurements. In addition, this double determination provides redundancy in case of failure of an element used in the method.

In one embodiment of the method the plurality of values may be determined by calculation on the basis of direct measurement by a remote pressure sensor in fluid communication with the patient's nostril(s). The pressure sensor may be arranged in or near a proximal end of a nasal cannula of which the distal end(s) are inserted into the patient's nostrils. In this embodiment the part of the nasal cannula between the pressure sensor and the nostril may serve as an obstacle to the airflow causing the detectable pressure difference.

In another embodiment of the method the plurality of values may be determined by direct measurement using a pressure sensor arranged in the patient's nostril(s). This allows a more compact set-up which may be more comfortable for the patient.

Steps b) and c) of the method may be performed at a location that is remote from the patient, and the plurality of values for the pressure difference may be transmitted to the remote location. Processing the series of pressure differences to derive the scaled respiratory flow rate and volume may require bulky and power-consuming equipment that needs to be kept away from the patient. The data transmission may be wireless or wired, depending on the circumstances.

In an embodiment of the method step a) may be performed for a plurality of breathing cycles during tidal breathing of the patient, and derivation of the scaled respiratory flow rate in step b) and derivation of the scaled respiratory volume in step c) for each separate cycle may include the use of the values for the pressure difference determined during the plurality of breathing cycles. In this way a difference between inhaled and exhaled volume is averaged out over the breathing cycles and more accurate curves are expected.

The first generalized relationship used in step b) to derive the scaled respiratory flow rate Q may be:

$$\tilde{Q}(t) = \begin{cases} \dfrac{|\Delta p|^b \langle T \rangle}{\langle I_{in} \rangle}, & \Delta p < 0 \\[2ex] \dfrac{|\Delta p|^b \langle T \rangle}{\langle I_{ex} \rangle}, & \Delta p \geq 0 \end{cases}$$

in which:

$$I_{in}(t) \equiv \int_0^{\tau} \min(0, \text{sign}(\Delta p))|\Delta p|^b d\tau \leq 0,$$

and:

$$I_{ex}(t) \equiv \int_0^{\tau} \max(0, \text{sign}(\Delta p))|\Delta p|^b d\tau \geq 0,$$

with $\langle I_{ex} \rangle = I_{ex}(T)/K$, $\langle I_{in} \rangle = I_{in}(T)/K$, where K is the number of breathing cycles and T the time to complete the series of K breathing cycles, and in which $\Delta p$ is the pressure difference and b is a constant which depends on the sign of $\Delta p$. In this way the scaled respiratory flow rate at each moment in time is determined as a function of the pressure difference only. Using this relationship the determination is independent of the patient or of the specific arrangement of the equipment used to perform the method.

The second generalized relationship used in step c) to derive the scaled respiratory volume V may be:

$$\tilde{V}(t) = \frac{I_{ex}(t)}{\langle I_{ex} \rangle} - \frac{I_{in}(t)}{\langle I_{in} \rangle}$$

in which $I_{ex}$, $I_{in}$, $\langle I_{ex} \rangle$ and $\langle I_{in} \rangle$ have the same meaning as above.

In an embodiment of the method the derivations in steps b) and c) are performed by a computer. Using a computer allows the data collected during step a) to be quickly and easily processed.

Summarizing the above, the method of the invention involves measuring a pressure, which need not be a static or dynamic pressure, applying a non-linear relationship between pressure and flow, applying mass conservation over a plurality of breathing cycles, and deriving ratio of proportionality constants or non-linear aerodynamic resistances.

The method described above allows pressures and flow rates to be determined independently of the geometry of the flow channel, which is important since this geometry is defined to a large extent by the shape of the patient's nostril. The method involves the use of pressure data collected in a wide interval around a specific time instant for computing a ratio of aerodynamic inspirational resistance to aerodynamic expirational resistance. In this way the method is self-calibrating. Eventually, the method leads to the derivation of a time-dependent and case-specific ratio of non-linear aerodynamic resistances for inspiration and expiration.

The invention further relates to a system for carrying out the method described above. In accordance with the invention such a system for determining a scaled respiratory flow rate and volume during respiration of a patient comprises:

a determination module configured for successively determining a plurality of values for a difference between a pressure in at least a first location in an upper respiratory tract of the patient and a reference pressure;

a first derivation module configured for deriving the scaled respiratory flow rate from the plurality of values for the pressure difference by using a first relationship;

a second derivation module configured for deriving the scaled respiratory volume from the plurality of values for the pressure difference by using a second relationship; and a display module for displaying the scaled respiratory flow rate and the scaled respiratory volume or a further variable derived from the scaled respiratory flow rate and volume in a graphical representation;

wherein the determination module is configured to be operative during tidal breathing of the patient.

Further embodiments of this system are disclosed herein.

The invention will now be described by way of some exemplary embodiments thereof, wherein reference is made to the annexed drawings, in which similar elements are identified by identical reference numerals, and in which.

Figure 5:
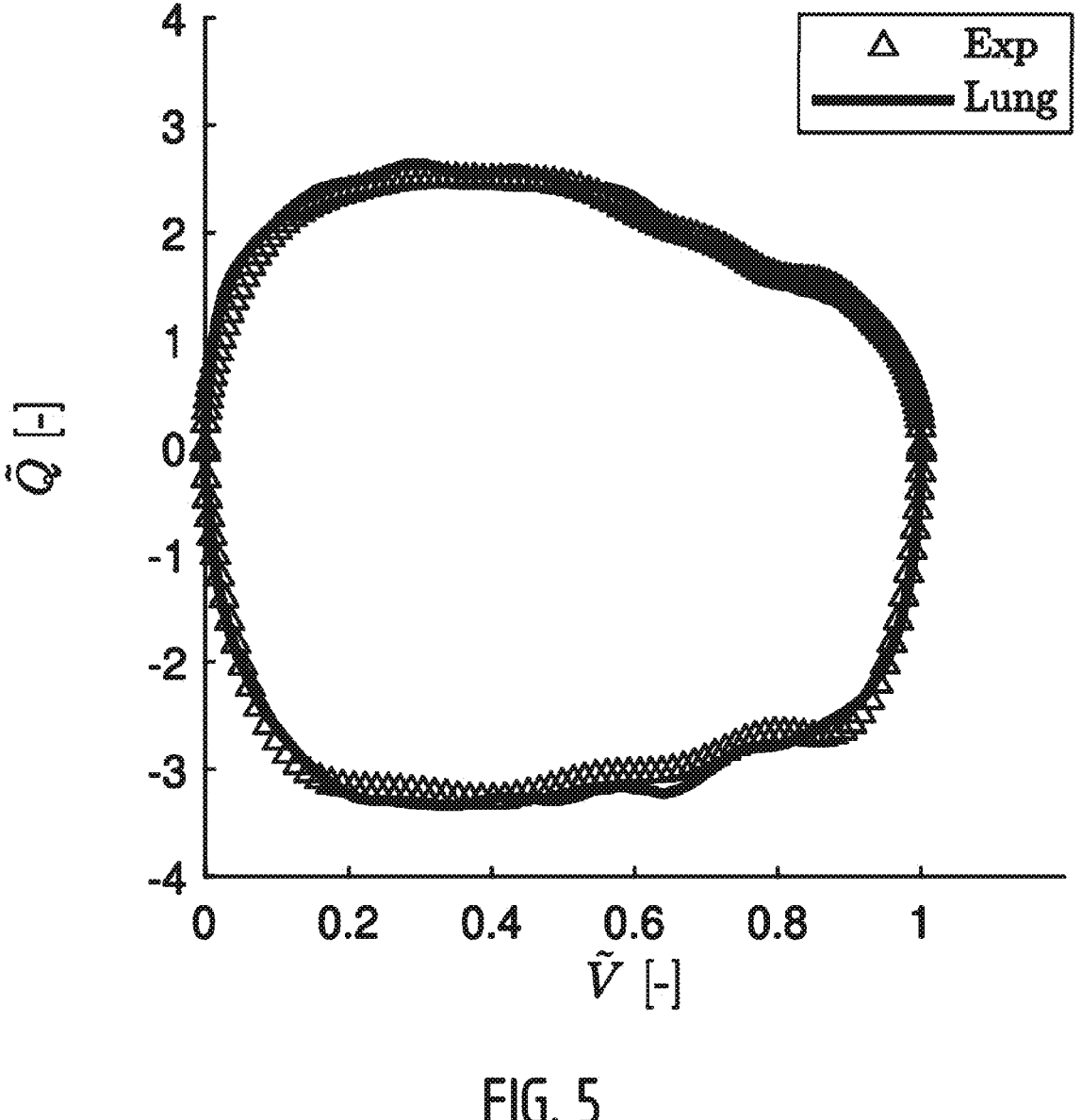
FIG. 5 shows graphical representations of scaled respiratory flow rates in relation to scaled respiratory volumes for an infant, comparing results of the method of the invention with experimental results.
Figure 6:
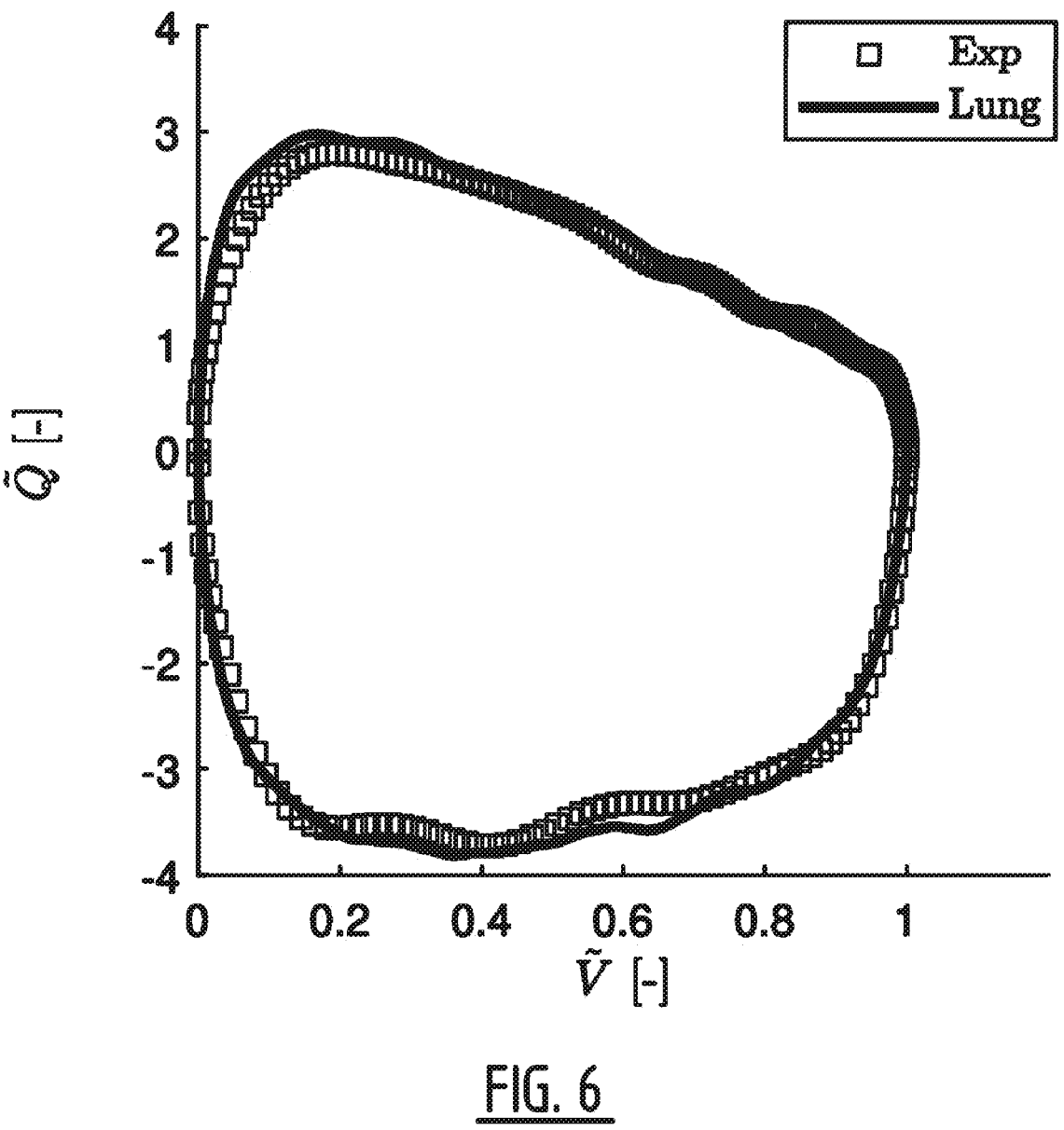
Figure 7:
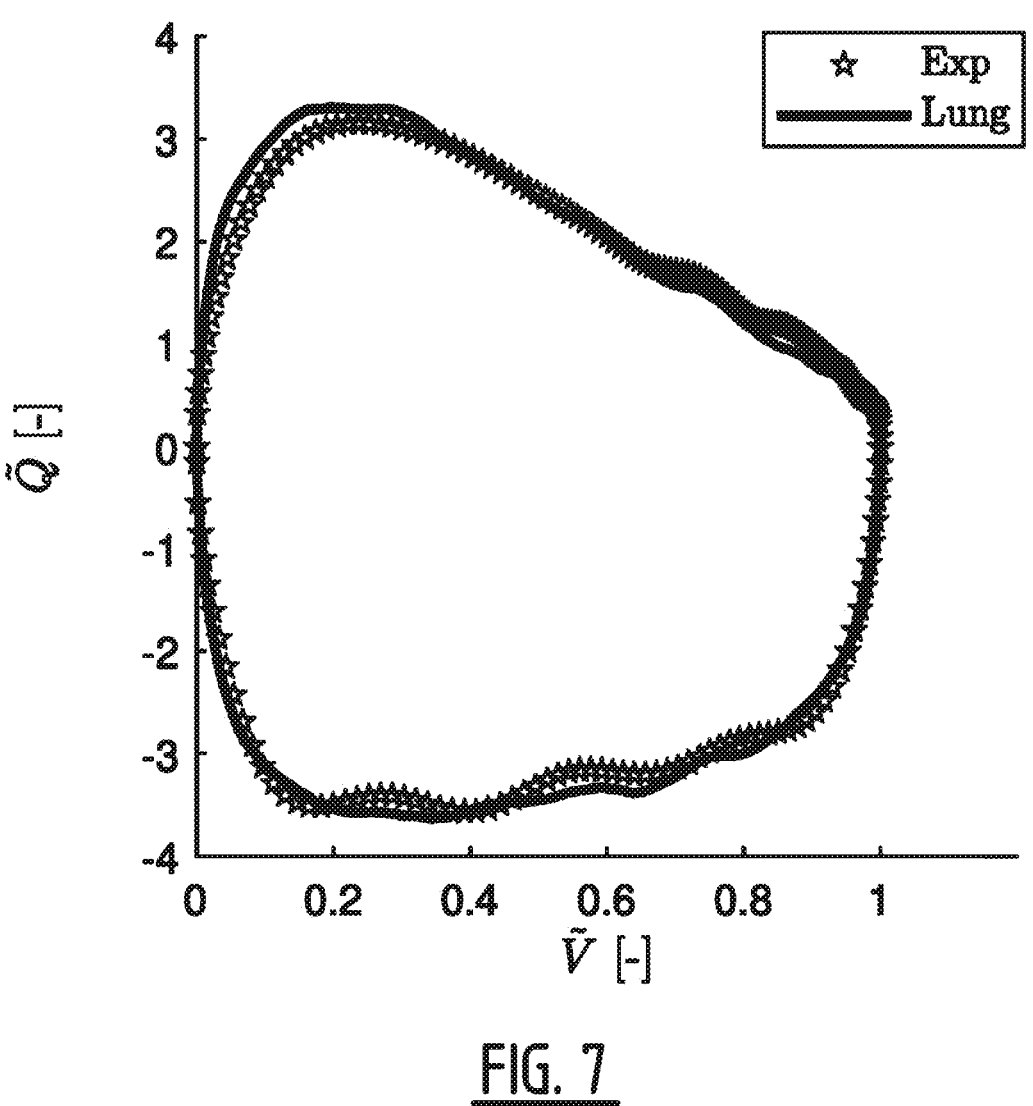

FIG. 6 corresponds with FIG. 5 but shows the results for an infant having moderately obstructed airways; and FIG. 7 corresponds with FIGS. 5 and 6 but shows the results for an infant having severely obstructed airways.

The novel concept underlying the present application is to use a difference between a pressure at a predetermined location in the upper respiratory tract of a patient—e.g. in the nostrils—and ambient pressure to estimate the flow rate and the exhaled volume. The pressure difference is caused either by resistance of a flow channel between the nostrils and cannula tubes or by an obstacle placed in the nostrils. For inhalation and exhalation separately, the flow-rate is estimated up to two constants: a proportionality constant and an exponent. Then, by scaling the flow-rate, only the ratio of the two proportionality constants remains, and by requiring that the net exhaled volume is zero after sufficiently many breathing cycles, the ratio can is computed. Finally, the values of the two exponents are conveniently estimated in the range 0.5-1.0, depending on whether the flow corresponds to inhalation or exhalation.

Upon inspiration, the flow towards each nostril is similar to that of a negative point source with radially oriented streamlines. At the nostrils' entrances the pressure is equal to ambient pressure, and to overcome aerodynamic friction, the pressure at the exits of the cannula tubes is lower than ambient pressure. Upon expiration, the flow leaves the nostrils like two approximately annular jets and again the pressure at the nostrils' exits is equal to ambient pressure. To overcome aerodynamic friction, the pressure at the exits of the cannula tubes in this case is higher than ambient pressure. The aerodynamic resistance in both cases is different because during inspiration the flow coming from ambient conditions is approximately laminar, but during expiration the flow coming from the lungs is turbulent.

Once a flow rate estimate is formally obtained, it is integrated over time to obtain a corresponding volume change. The proportionality constant in the flow rate is eliminated from the expressions for the flow rate and the volume change upon proper scaling. This leads to a scaled flow-volume curve which can be shown to have the same shape as the (unknown) non-scaled flow-volume curve. From a clinical point of view this is very relevant since it is primarily the shape that is used to assess the health status of a patient, whereas the dimensions of the flow-volume curve are of secondary interest.

Figure 1:
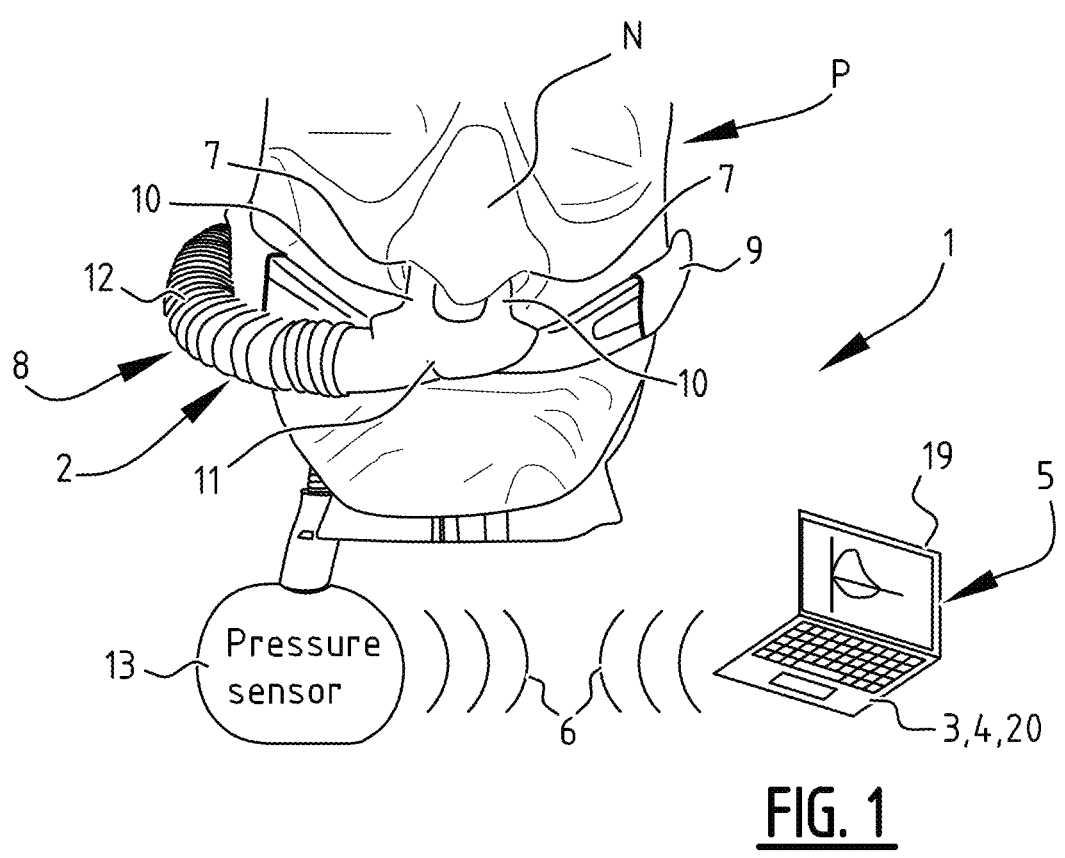
FIG. 1 is a schematic illustration of a first embodiment of the system of the invention.

A system 1 for determining a scaled respiratory flow rate and volume during respiration of a patient P comprises a determination module 2, a first derivation module 3, a second derivation module 4 and a display module 20 (FIG. 1). In the illustrated embodiment the first and second derivation modules 3, 4 and the display module 20 are at a location that is remote from the patient P and form part of a computer 5. Each derivation module 3, 4 may be embodied as hardware, firmware or software. In the illustrated embodiment the first and second derivation modules 3, 4 are software programs running on the computer 5. The display module 20 comprises a software program running on the computer 5 and a screen 19 of the computer. The computer 5 is connected to the determination module 2 for allowing communication and data exchange between the determination module 2 and the first and second derivation modules 3,

4. The connection 6 between the computer 5 and the determination module 2 is shown here to be a wireless connection, but could also be a wired connection.

The determination module 2 is configured for successively determining a plurality of values for a difference $\Delta p$ between a pressure $p_a$ in at least a first location in an upper respiratory tract of the patient P and a reference pressure $p_{ref}$ during tidal breathing of the patient. The first location may be a location in one of the nostrils 7 of the patient P. In the illustrated embodiment the reference pressure is ambient pressure $p_{amb}$. The first derivation module 3 is configured for deriving the scaled respiratory flow rate Q from the plurality of values for the pressure difference $\Delta p$ by using a first relationship. And the second derivation module 4 is configured for deriving the scaled respiratory volume V from the plurality of values for the pressure difference $\Delta p$ by using a second relationship.

In this embodiment the determination module comprises a nasal cannula 8 which may be attached to the patient's head by a strap 9. The nasal cannula 8 has two prongs 10, the ends of which are inserted into respective nostrils 7 of the patient P. Each prong 10 debouches in a plenum 11, which in turn is connected to a collective tube 12 having a pressure sensor 13 connected to its proximal end 14. The proximal end 14 of the tube 12 is not connected to any ventilation device, since the nasal cannula 8 merely serves to create aerodynamic resistance to the airflow when the patient P breathes through the nasal cannula 8. The pressure sensor 13 measures a pressure $p_b$ at the proximal end of the tube 12. Since the nasal cannula 8 is closed at its proximal end, there is no flow through the nasal cannula 8 and the patient P breathes only through the flow paths through his nostrils 7 which are left free by the prongs 10 of the cannula 8. Consequently, the pressure $p_b$ as measured at the proximal end of tube 12 has the same value as the pressure $p_a$ at the entry/exit of the prongs 10 in the nostrils 7.

The difference $\Delta p$ between the pressure $p_a$ at the distal end of the nasal cannula 8, i.e. in the nostrils 7, and the ambient pressure $p_{amb}$ is transmitted to the first and second derivation modules 3, 4. In these first and second derivation modules 3, 4 the absolute value of this pressure difference $\Delta p$ is then used to derive both the scaled respiratory flow rate Q and the scaled respiratory volume V of the patient during tidal breathing, as will be shown below.

Figure 2:
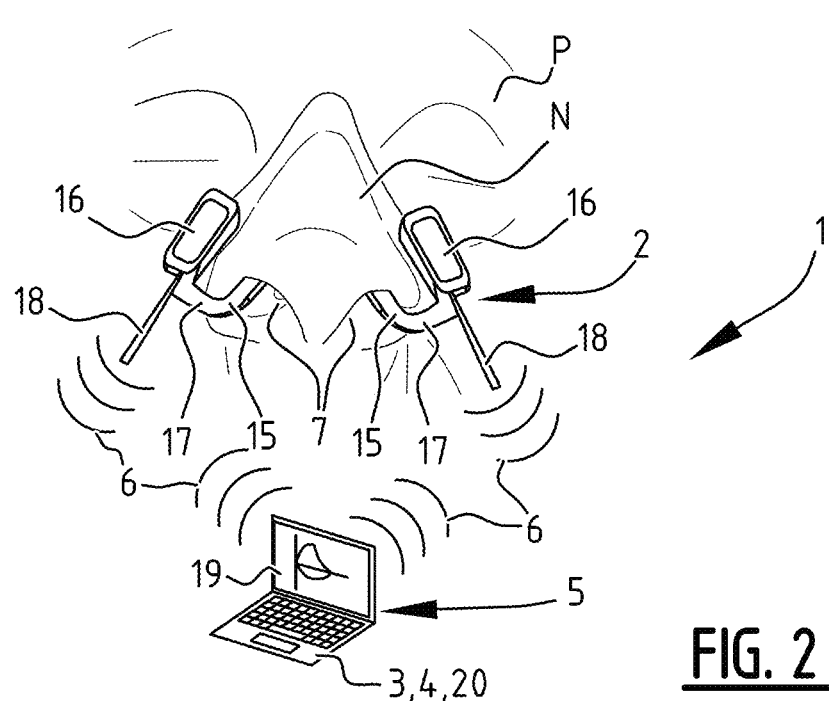
FIG. 2 is a schematic illustration of a second embodiment of the system of the invention.

In an alternative embodiment of the system 1 the determination module 2 comprises two separate obstacles 15, which are each arranged in one of the nostrils 7 of the patient P (FIG. 2). Each obstacle 15 also carries a pressure sensor (not shown) which provides pressure signals representative for the pressure $p_a$ inside the nostril 7 to a transceiver 16 arranged outside the nostril 7. The obstacle 15 and the transceiver 16 may be connected by a flexible bridge piece 17, which allows the combination of obstacle and transceiver to be clamped onto the nose N of the patient P. The determination module 2 further comprises a sensor (not shown) for measuring the ambient pressure $p_{amb}$. This ambient pressure sensor may be arranged anywhere outside the patient, e.g. on the transceiver 16.

In the illustrated embodiment the transceivers 16 are wireless transceivers, which include antennas 18 to send the pressure signals to the first and second derivation modules 3, 4. The pressure signals may be representative of the pressure difference $\Delta p$ that is determined in the determination module 2. Alternatively, the pressure signals sent to the computer 5 may be representative for pressures $p_a$ and $p_{amb}$, from which a program in the computer 5 may calculate values for the pressure difference $\Delta p$ which may then be input to the first and second derivation modules 3, 4.

These derivation modules are again embodied as software programs in the computer 5. It should be noted that the computer 5 also includes a master program controlling the operation of both the determination module 2 and the derivation modules 3, 4. This master program causes the computer 5 to send control signals to the transceivers 16 of the determination module 2, so as to start or stop a series of readings of the pressure in the nostrils 7. Consequently, both the computer 5 and the transceivers 16 are arranged for two-way communication. The same applies to the communication between the pressure sensor 13 and the computer 5 in the first embodiment. Normally, the system will be operated for some time so as to allow sufficient pressure measurements to be performed over a substantial number of breathing cycles.

The first and second derivation modules 3, 4 may derive momentary values for the scaled respiratory flow rate Q and the scaled respiratory volume V from the pressure differences determined by the determination module 2. In order to obtain a graphical representation of the scaled respiratory flow rate and volume which is easy to analyze the flow rate and volume may be scaled as follows.

For a given flow rate Q(t), defined positive when exhaling, the net exhaled volume V(t) is $$V(t) = \int_0^\tau Q(\tau)d\tau.$$

This expression can be split into a negative part related to pure inhalation and a positive part related to pure exhalation:

$$V(t)=V_{in}(t)+V_{ex}(t)$$

with the two parts defined as:

$$V_{in}(t) \equiv \int_0^\tau \min(0, Q(\tau))d\tau \le 0,$$

$$V_{ex}(t) \equiv \int_0^\tau \max(0, Q(\tau))d\tau \ge 0.$$

Now, T is defined as the total time of K breathing cycles:

$$T \equiv \sum_{i=1}^K T_i$$

The cycle-averaged increment of any function f(t) is defined as:

$$\langle f \rangle = \frac{f(T)}{K}.$$

By dividing the net exhaled volume V(t) by $\langle V_{ex} \rangle$, one arrives at an expression for the scaled volume:

$$\tilde{V}(t) = \frac{V_{ex}(t) + V_{in}(t)}{\langle V_{ex} \rangle}.$$

Similarly, the flow rate can be scaled as:

$$\tilde{Q}(t) \equiv \frac{Q(t)\langle T \rangle}{\langle V_{ex} \rangle}$$

with $\langle T \rangle$ the average cycle time (i.e. T/K).

Figure 3:
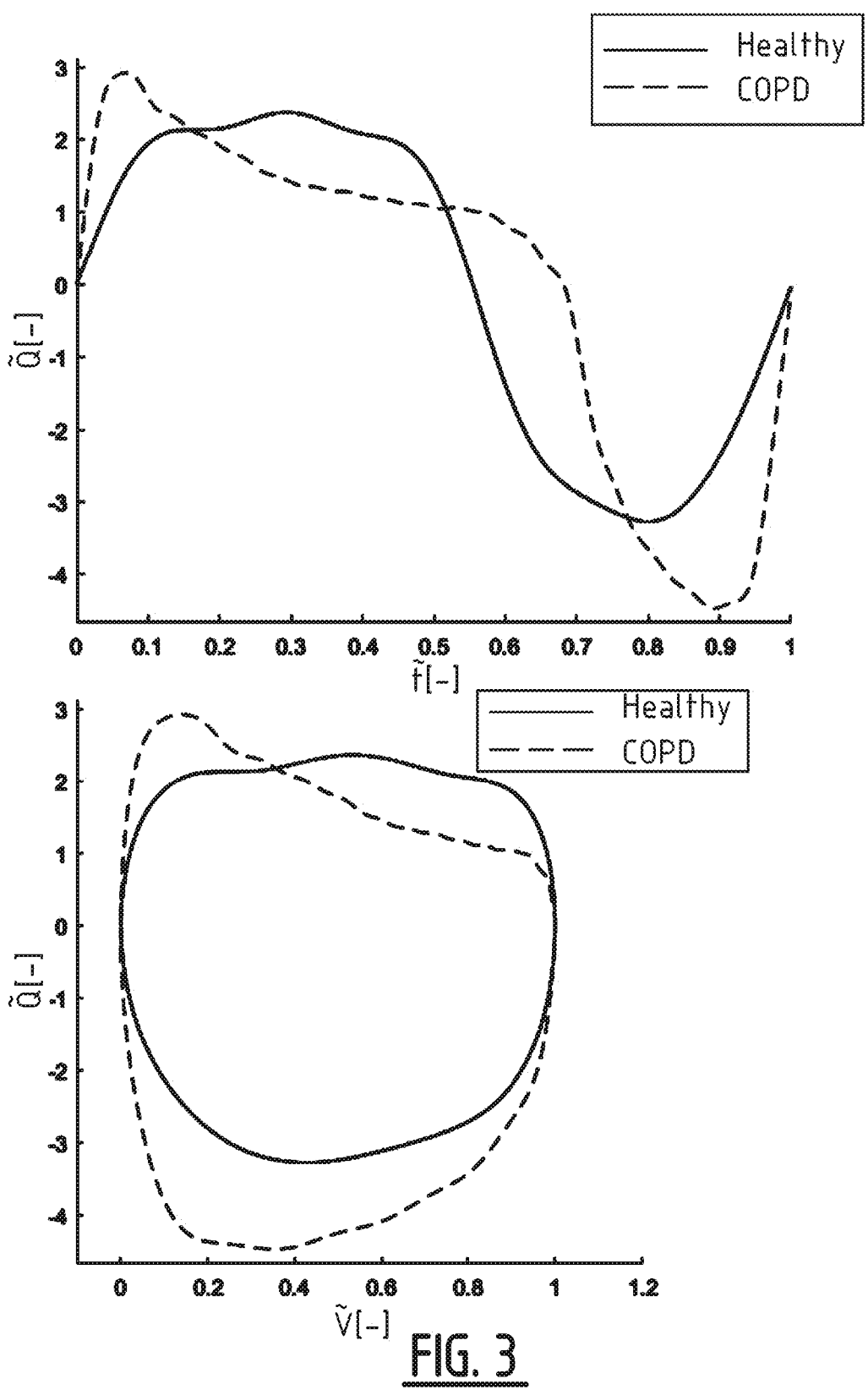
FIG. 3 shows graphical representations of scaled respiratory flow rates of an adult both as a function of time (upper graph) and in relation to scaled respiratory volume (lower graph)
Figure 4:
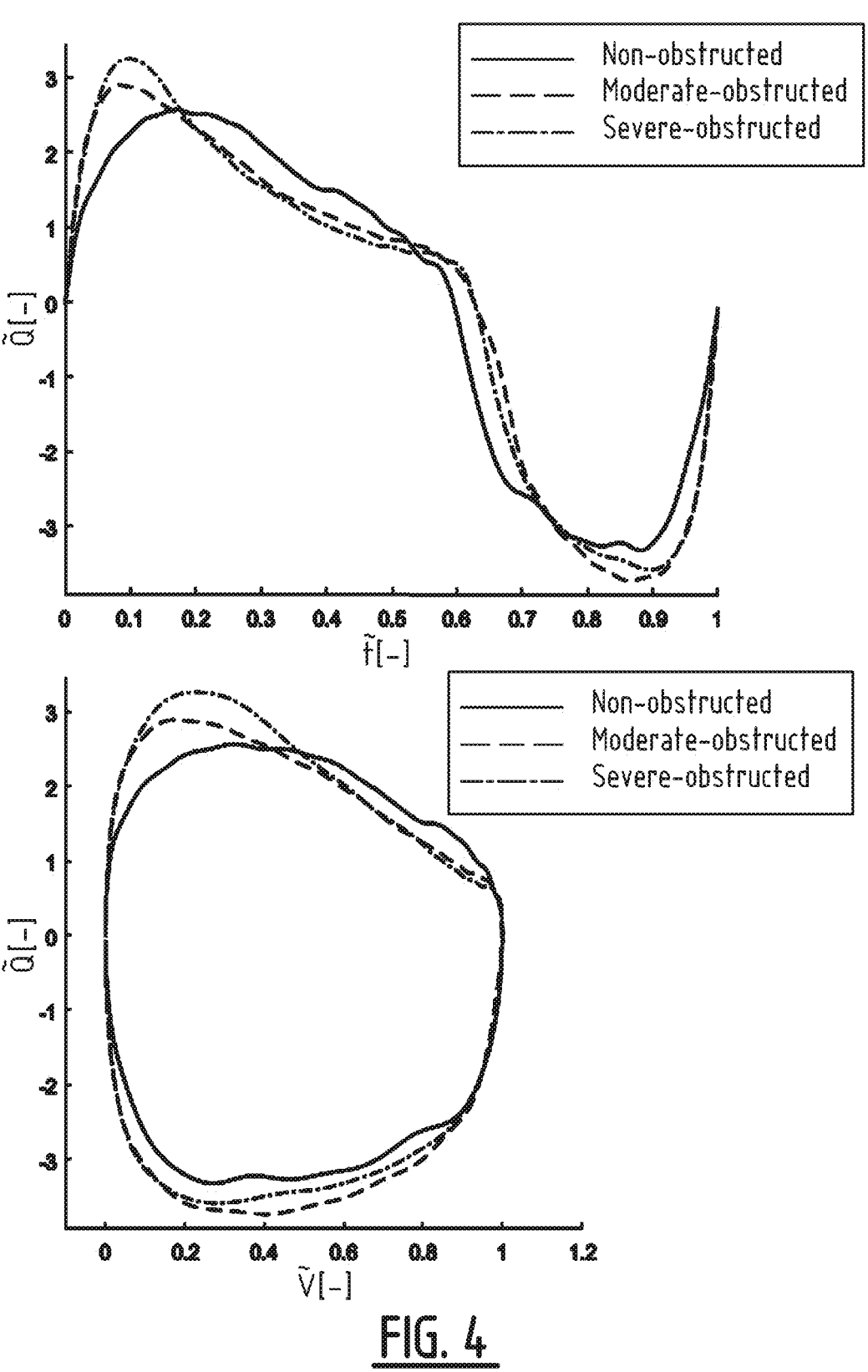
FIG. 4 shows similar graphical representations as FIG. 3, but relating to an infant.

The scaled flow rate Q as a function of time in accordance with the above equation is graphically represented in the upper graphs of FIGS. 3 and 4. The upper graph of FIG. 3 relates to an adult and has a tidal volume of 450 ml and a length of 4 s. The solid line shows the scaled respiratory flow rate for a healthy adult and the dashed line the flow rate for an adult suffering from COPD. The upper graph of FIG. 4 relates to an infant and has a tidal volume of 85 ml and a length of 2 s. This graph shows three curves, a solid line representing non-obstructed breathing, a dashed line representing moderately obstructed breathing and a dash-dotted line representing severely obstructed breathing.

The lower graphs of FIGS. 3 and 4 show graphic representations of the scaled flow rate Q in accordance with the above equation in relation to the scaled volume V in accordance with its relevant equation represented above..

Here again, FIG. 3 relates to an adult and shows a flow-volume curve of a healthy adult in solid lines and a flow-volume curve of a COPD patient in dashed lines. From this figure the differences in shape are immediately evident, and provide a clear indication of the state of the patient. The downwardly sloping upper part of the flow-volume curve, which represents the exhalation phase of the breathing cycle, is typical of a patient suffering from COPD, while the flow-volume curve for a healthy adult has a far more regular, in fact almost circular shape. Other respiratory disorders may lead to different shapes of flow-volume curves than COPD, e.g. a flow-volume curve having a flat top, but they can always be distinguished from flow-volume curves of healthy patients.

Similar differences can be observed between the shape of the flow-volume curve for unobstructed breathing of an infant shown in solid lines in FIG. 4, and the shapes of the flow-volume curves for obstructed breathing. The more severe the obstruction, the more pronounced the downward slope of the exhalation phase at the top of the curve.

The derivation of the scaled respiratory flow rate Q from the pressure difference $\Delta p$ in the first derivation module 3 and the derivation of the scaled respiratory volume V from the pressure difference $\Delta p$ in the second derivation module 4 may be done as follows.

From a fluid mechanics point of view, the flow rate Q and the pressure difference $\Delta p$ for a given flow tube are interdependent. In this work, the following functional relationship is assumed:

$$Q(\Delta p)=a|\Delta p|^b, \ \text{sign}(a)=\text{sign}(\Delta p).$$

The constants a and b both depend on the sign of $\Delta p$, $$a(\text{sign}(\Delta p)), \ b(\text{sign}(\Delta p)),$$

which reflects that the aerodynamic resistance not only depends on the geometry of the flow channel, but also on the direction of the flow and on the upstream flow condition. For example, when the flow is fully laminar b=1, and when the flow is fully turbulent $$b = \frac{1}{2}.$$

As a result of the above two equations, only the ratio of a(−) and a(+) appears in the expression for Ṽ(t). Hence, upon defining the following integrals, $$I_{in}(t) \equiv \int_0^t \min(0, \operatorname{sign}(\Delta p))|\Delta p|^b d\tau \le 0,$$

$$I_{ex}(t) \equiv \int_0^t \max(0, \operatorname{sign}(\Delta p))|\Delta p|^b d\tau \ge 0,$$

the scaled volume becomes $$\tilde{V}(t) = \frac{I_{ex}(t)}{\langle I_{ex} \rangle} - \frac{a(-)}{a(+)} \frac{I_{in}(t)}{\langle I_{ex} \rangle}$$

with $\langle I_{ex} \rangle = I_{ex}(T)/K$, $\langle I_{in} \rangle = I_{in}(T)/K$, and $\langle T \rangle = T/K$, with K the number of cycles taken into account, and T the time needed to complete these breathing cycles.

By assuming that after K cycles the net inhaled volume equals the nett exhaled volume, such that $$\tilde{V}(T)=0,$$

the ratio of the constants a can be calculated as:

$$\frac{a(-)}{a(+)} = \frac{I_{ex}(T)}{I_{in}(T)} = \frac{\langle I_{ex} \rangle}{\langle I_{in} \rangle}$$

Substituting this expression into the equation for the scaled volume gives:

$$\tilde{V}(t) = \frac{I_{ex}(t)}{\langle I_{ex} \rangle} - \frac{I_{in}(t)}{\langle I_{in} \rangle}.$$

Similarly, the scaled flow rate can be calculated as:

$$\tilde{Q}(t) = \begin{cases} \dfrac{|\Delta p|^b \langle T \rangle}{\langle I_{in} \rangle}, & \Delta p < 0 \\[2ex] \dfrac{|\Delta p|^b \langle T \rangle}{\langle I_{ex} \rangle}, & \Delta p \ge 0 \end{cases}$$

As all expressions above include only variables which are characteristics of parts of the system, they do not depend on the actual patient for whom the flow-volume curves are to be established. Therefore, these expressions denote generalized relationships which are valid for all patients. Consequently, the method and system can be applied universally, which greatly increases their utility. Moreover, since the method and system of the invention do not have to be adapted to different patients, they are easy to use and do not require extensive training

Experimental Method

In order to test which phase diagram (i.e. which flow behaviour) best reflects the shape of actual flow-volume curves or "loops", in-vitro experiments were performed using an anatomically accurate 3D-printed upper airway geometry and Fisher & Paykel nasal cannulae. The upper-airway geometry used is known as the SAINT-model, a 9 month old Caucasian girl. In the model, the oral airway was closed for air passage. The model ended at the trachea, where a lung simulator, consisting of a linear motor rigidly connected to a pneumatic cylinder, was connected. The linear motor (LinMot PS01-48×240-C) was controlled by a servo drive (LinMot E1100-GP-HC), which in turn was controlled using the LinMot Talk 6.8 software. Different representative breathing cycles were prescribed, namely a non-obstructed pattern, a moderately obstructed pattern and a severely obstructed pattern. The determined scaled flow-time curves that were prescribed to the pump, and the resulting scaled flow-volume curves, are the ones shown in FIG. 4 and discussed above. The profiles were determined by applying image analysis to figures found in relevant literature. The data was approximated by a Fourier series, such that the curve was closed and smoothed. After that, the curve was scaled to match the desired (chosen) tidal volume and cycle length.

In the same way two profiles relevant for adults have been derived: a healthy and a COPD-profile. The scaled flow-time curves and scaled flow-volume loops are shown in FIG. 3. These profiles are not yet used for experiments, but indicate the relevance of the shape of scaled tidal spirometric curves in adults.

Preliminary Results

In order to verify the method, experiments were conducted on the 3D-printed infant upper airway geometry. From the recorded pressure-time signal, separate breathing cycles were identified and the phase diagrams were calculated from this pressure-time signal using b(+)=0.5 and b(−)=0.8. In FIGS. 5-7, the resulting phase diagrams have been plotted together with the reference profiles as prescribed by the pump. Here FIG. 5 represents the phase diagram or flow-volume curve for an infant having a non-obstructed breathing cycle, while FIGS. 6 and 7 represent a moderately obstructed and severely obstructed breathing cycle, respectively. In all three figures the solid line represents the input patterns, whereas the collection of separate data points represents the experimental results. It is seen that reconstructed and prescribed phase diagrams are in very good agreement, and that the characteristic shapes of the different breathing profiles is clearly observed.

In the system 1 of the invention the phase diagrams or flow-volume curves discussed above are generated by the display module 20 and shown on the screen 19 of the computer 5. Alternatively or additionally the phase diagrams or flow-volume curves may be sent to a printer (not shown). Either the on-screen display or the print-out may then be analysed by a physician, who may compare the flow-volume curve with a standard or ideal flow-volume curve and may identify possible anomalies to determine if a patient is suffering from a respiratory disorder. Such analysis may be performed on-site, i.e. at the location where the pressure measurements are taken, or remotely. The computer 5 may be programmed to send the flow-volume curves to a physician at a remote location, e.g. a hospital or clinic, for further analysis. In this way a patient's health may be monitored remotely.

Instead of on a computer, the first and second derivation modules 3, 4 and the display module 20 could be programmed in an app to be downloaded on a handheld device like e.g. a smartphone or a wearable like e.g. a smartwatch. In this way the pressure measurements could be used for home testing, and the results of such tests could lead to a patient being called to a hospital for further testing if his flow-volume curve would show an anomaly.

In this way the invention provides a method and system which allows flow-volume curves or spirometric curves to be obtained during tidal breathing of a patient, without having to resort to the use of a catheter. The method of the invention forms an improvement over prior art methods like spirometry or pneumotachography.

Although the method and system of the invention have been described above by reference to some exemplary embodiments thereof, it will be clear that the invention is not limited thereto. The method and system may be adapted in various ways within the scope of the appended claims.

The invention claimed is:

1. A method for determining a scaled respiratory flow rate and volume during respiration of a patient, comprising the steps of:

a) using a pressure sensor located in or near a nasal cannula in fluid communication with the patient's nostril to collect pressure measurements in at least a first location in an upper respiratory tract of the patient, and successively determining a plurality of values for a difference between a pressure in at least the first location in the upper respiratory tract of the patient and a reference pressure, wherein the first location in the upper respiratory tract is in a nostril of the patient and wherein the reference pressure is ambient pressure;

b) deriving the scaled respiratory flow rate from the plurality of values for the pressure difference by using a first relationship;

c) deriving the scaled respiratory volume from the plurality of values for the pressure difference by using a second relationship; and d) displaying the scaled respiratory flow rate derived in step b) and the scaled respiratory volume derived in step c) or a further variable derived from the scaled respiratory flow rate and volume in a graphical representation;

wherein step a) is performed during tidal breathing of the patient; and wherein an end of a prong of a nasal cannula is arranged in the upper respiratory tract before step a) is performed, the end of the cannula prong being arranged in the nostril between the first location and a nostril entry to create aerodynamic resistance or cause a local narrowing of the respiratory tract to increase the pressure differences.

2. The method of claim 1, wherein the scaled respiratory flow rate and scaled respiratory volume are displayed in a single graph, and optionally wherein the first and second relationships used in steps b) and c) are each generalized relationships which are substantially independent of the patient.

3. The method of claim 1, wherein there is a first location in each of the patient's nostrils and wherein a first plurality of values for the pressure difference is determined in one of the patient's nostrils and a second plurality of values for the pressure difference is determined in the other nostril.

4. The method of claim 1, wherein the pressure sensor is arranged in a collective tube connected to a proximal end of the nasal cannula, the nasal cannula also having a distal end inserted into the patient's nostrils.

5. The method of claim 1, wherein at least one of:

steps b) and c) are performed at a location that is remote from the patient, and wherein the plurality of values for the pressure difference is transmitted to the remote location; and step a) is performed for a plurality of breathing cycles during tidal breathing of the patient, and wherein derivation of the scaled respiratory flow rate in step b) and derivation of the scaled respiratory volume in step c) for each separate cycle include the use of the values for the pressure difference determined during the plurality of breathing cycles.

6. The method of claim 2, wherein the first generalized relationship used in step b) to derive the scaled respiratory flow rate is:

$$\tilde{Q}(t) = \begin{cases} \dfrac{|\Delta p|^{b}\langle T\rangle}{\langle I_{in}\rangle}, & \Delta p < 0 \\[2mm] \dfrac{|\Delta p|^{b}\langle T\rangle}{\langle I_{ex}\rangle}, & \Delta p \geq 0 \end{cases}$$

in which:

$$I_{in}(t) \equiv \int_{0}^{\tau} \min(0, \mathrm{sign}(\Delta p))|\Delta p|^{b} d\tau \leq 0,$$

$$I_{ex}(t) \equiv \int_{0}^{\tau} \max(0, \mathrm{sign}(\Delta p))|\Delta p|^{b} d\tau \geq 0,$$

and $\langle I_{ex}\langle = I_{ex}(T)/K$, $\langle I_{in}\langle = I_{in}(T)/K$, and $\langle T\langle = T/K$, with K the number of breathing cycles taken into account, T the time needed to complete these breathing cycles, and in which $\Delta p$ is the pressure difference and b is a constant which depends on the sign of $\Delta p$.

7. The method of claim 2, wherein the second generalized relationship used in step c) to derive the scaled respiratory volume is:

$$\tilde{V}(t) = \frac{I_{ex}(t)}{\langle I_{ex}\rangle} - \frac{I_{in}(t)}{\langle I_{in}\rangle}.$$

with $\langle I_{ex}\langle = I_{ex}(T)/K$, $\langle I_{in}\langle = I_{in}(T)/K$, and $\langle T\langle = T/K$ with K the number of cycles taken into account, and T the time needed to complete these breathing cycles.

8. The method of claim 1, wherein the derivations in steps b) and c) and/or the displaying in step d) are/is performed by a computer.

9. A system for determining a scaled respiratory flow rate and volume during respiration of a patient, comprising:

a determination module comprising a pressure sensor located in or near a nasal cannula in fluid communication with the patient's nostril to collect pressure measurements in at least a first location in an upper respiratory tract of the patient, the determination module configured for successively determining a plurality of values for a difference between a pressure in at least the first location in the upper respiratory tract of the patient and a reference pressure, the determination module being configured for determining the pressure differences between a first location in a nostril of the patient and ambient pressure;

a first derivation module comprising a first processing circuit configured for deriving the scaled respiratory flow rate from the plurality of values for the pressure difference by using a first relationship;

a second derivation module comprising a second processing circuit configured for deriving the scaled respiratory volume from the plurality of values for the pressure difference by using a second relationship; and a display module comprising a display configured for displaying the scaled respiratory flow rate and the scaled respiratory volume or a further variable derived from the scaled respiratory flow rate and volume in a graphical representation;

wherein the determination module is configured to be operative during tidal breathing of the patient, and wherein the determination module comprises an end of a prong of a nasal cannula configured to be arranged in the upper respiratory tract, the end of the cannula prong being configured to be arranged in the nostril between the first location and a nostril entry to create aerodynamic resistance or cause a local narrowing of the respiratory tract to increase the pressure differences.

10. The system of claim 9, wherein the display module is configured to display the scaled respiratory flow rate and scaled respiratory volume in a single graph, and optionally wherein the first and second determination modules are each configured for using generalized relationships which are substantially independent of the patient.

11. The system of claim 9, wherein there is a first location in each of the patient's nostrils and wherein the determination module is configured for determining a first plurality of values for the pressure difference in one of the patient's nostrils and a second plurality of values for the pressure difference in the other nostril.

12. The system of claim 9, wherein the pressure sensor is arranged in a collective tube connected to a proximal end of the nasal cannula, the nasal cannula also having a distal end inserted into the patient's nostrils.

13. The system of claim 9, wherein at least one of:

the first and second derivation modules are at a location that is remote from the patient and are connected to the determination module for receiving the plurality of values for the pressure difference; and the determination module is configured for determining the plurality of values for the pressure difference for a plurality of breathing cycles during tidal breathing of the patient, and wherein the first and second derivation modules are each configured for using, for each separate cycle, the values for the pressure difference determined during the plurality of breathing cycles.

14. The system of claim 10, wherein the first derivation module is configured to use the following relationship to derive the scaled respiratory flow rate:

$$\tilde{Q}(t) = \begin{cases} \dfrac{|\Delta p|^b \langle T \rangle}{\langle I_{in} \rangle}, & \Delta p < 0 \\[2mm] \dfrac{|\Delta p|^b \langle T \rangle}{\langle I_{ex} \rangle}, & \Delta p \ge 0 \end{cases}$$

in which:

$$I_{in}(t) \equiv \int_0^\tau \min(0, \operatorname{sign}(\Delta p))|\Delta p|^b d\tau \le 0,$$

$$I_{ex}(t) \equiv \int_0^\tau \max(0, \operatorname{sign}(\Delta p))|\Delta p|^b d\tau \ge 0,$$

and $\langle I_{ex} \langle = I_{ex}(T)/K$, $\langle I_{in} \langle = I_{in}(T)/K$, and $\langle T \langle = T/K$, with K the number of breathing cycles taken into account, T the time needed to complete these breathing cycles, and in which $\Delta p$ is the pressure difference and b is a constant which depends on the sign of $\Delta p$.

15. The system of claim 10, wherein the second derivation module is configured to use the following relationship to derive the scaled respiratory volume:

$$\tilde{V}(t) = \frac{I_{ex}(t)}{\langle I_{ex} \rangle} - \frac{I_{in}(t)}{\langle I_{in} \rangle}.$$

in which:

$$I_{in}(t) \equiv \int_0^\tau \min(0, \operatorname{sign}(\Delta p))|\Delta p|^b d\tau \le 0,$$

$$I_{ex}(t) \equiv \int_0^\tau \max(0, \operatorname{sign}(\Delta p))|\Delta p|^b d\tau \ge 0,$$

and $\langle I_{ex} \langle = I_{ex}(T)/K$, $\langle I_{in} \langle = I_{in}(T)/K$, and $\langle T \langle = T/K$, with K the number of breathing cycles taken into account, T the time needed to complete these breathing cycles, and in which $\Delta p$ is the pressure difference and b is a constant which depends on the sign of $\Delta p$.

16. The system of claim 9, wherein the first and second derivation modules and/or the display module form(s) part of a computer.

17. A method for determining a scaled respiratory flow rate and volume during respiration of a patient, comprising the steps of:

a) using a pressure sensor located in the patient's nostril to collect pressure measurements in at least a first location in an upper respiratory tract of the patient, and successively determining a plurality of values for a difference between a pressure in at least the first location in the upper respiratory tract of the patient and a reference pressure, wherein the first location in the upper respiratory tract is in a nostril of the patient and wherein the reference pressure is ambient pressure;

b) deriving the scaled respiratory flow rate from the plurality of values for the pressure difference by using a first relationship;

c) deriving the scaled respiratory volume from the plurality of values for the pressure difference by using a second relationship; and d) displaying the scaled respiratory flow rate derived in step b) and the scaled respiratory volume derived in step c) or a further variable derived from the scaled respiratory flow rate and volume in a graphical representation wherein step a) is performed during tidal breathing of the patient, and wherein an obstacle is arranged in the upper respiratory tract before step a) is performed, the obstacle being arranged in the nostril between the first location and a nostril entry to cause a local narrowing of the respiratory tract to increase the pressure differences.

18. The method of claim 17, wherein the pressure sensor is carried by the obstacle.

19. A system for determining a scaled respiratory flow rate and volume during respiration of a patient, comprising:

a determination module comprising a pressure sensor located in the patient's nostril to collect pressure measurements in at least a first location in an upper respiratory tract of the patient, the determination module configured for successively determining a plurality of values for a difference between a pressure in at least the first location in the upper respiratory tract of the patient and a reference pressure, the determination module being configured for determining the pressure differences between the first location in the nostril of the patient and ambient pressure;

a first derivation module comprising a first processing circuit configured for deriving the scaled respiratory flow rate from the plurality of values for the pressure difference by using a first relationship;

a second derivation module comprising a second processing circuit configured for deriving the scaled respiratory volume from the plurality of values for the pressure difference by using a second relationship; and a display module comprising a display configured for displaying the scaled respiratory flow rate and the scaled respiratory volume or a further variable derived from the scaled respiratory flow rate and volume in a graphical representation;

wherein the determination module is configured to be operative during tidal breathing of the patient, and wherein the determination module comprises an obstacle configured to be arranged in the upper respiratory tract, the obstacle being configured to be arranged in the nostril between the first location and a nostril entry to cause a local narrowing of the respiratory tract to increase the pressure differences.

20. The system of claim 19, wherein the obstacle carries the pressure sensor.

\* \* \* \* \*